United States Patent [19]
Scott et al.

[11] Patent Number: 5,549,634
[45] Date of Patent: Aug. 27, 1996

[54] SURGICAL INSTRUMENT WITH SWIVEL MEMBER

[75] Inventors: Tony D. Scott, Weatherford; Ray Umber, Arlington; William J. Vaughn, Fort Worth, all of Tex.

[73] Assignee: Midas Rex Pneumatic Tools, Inc., Fort Worth, Tex.

[21] Appl. No.: 316,925

[22] Filed: Oct. 3, 1994

Related U.S. Application Data

[63] Continuation-in-part of Ser. No. 958,229, Oct. 8, 1992, Pat. No. 5,352,234.

[51] Int. Cl.$^6$ ............... A61B 17/32; A61B 17/00
[52] U.S. Cl. ............. 606/170; 285/184; 433/133; 433/130; 606/90
[58] Field of Search ............ 606/1, 170, 180, 606/190; 285/184, 118, 81, 82, 84; 433/133, 130

[56] References Cited

U.S. PATENT DOCUMENTS

| | | |
|---|---|---|
| 647,010 | 4/1900 | Marshall . |
| 1,677,337 | 7/1928 | Grove . |
| 2,503,281 | 4/1950 | Lynch et al. ............... 285/184 |
| 2,557,507 | 6/1951 | Lang, Jr. ............... 287/14 |
| 2,886,262 | 5/1959 | Fletcher ............... 244/23 |
| 3,835,858 | 9/1974 | Hagen . |
| 3,847,154 | 11/1974 | Nordin . |
| 4,055,185 | 10/1977 | Waldron . |
| 4,071,029 | 1/1978 | Richmond et al. . |
| 4,281,989 | 8/1981 | Glover et al. ............... 433/130 |
| 4,738,476 | 4/1988 | Peaster ............... 285/178 |
| 4,747,406 | 5/1988 | Nash . |
| 4,827,615 | 5/1989 | Graham ............... 30/166 |

*Primary Examiner*—Tamara L. Graysay
*Attorney, Agent, or Firm*—James E. Bradley; Mark D. Perdue

[57] ABSTRACT

A surgical instrument includes a conduit, the conduit having a conduit axis defined through a terminal end thereof, and a fluid-powered motor for rotating a dissecting tool, the motor having a longitudinal motor axis. A swivel member is connected in fluid communication between the motor and the conduit. The swivel member comprises a motor portion including a motor face inclined at a selected angle from the motor axis, and a conduit portion including a conduit face arranged oppositely that of the motor face and formed to engage matingly with the motor face. A connection shaft extends from one of the motor face and the conduit face and is engaged rotatably with a connection receptacle formed in another of the motor face and the conduit face. The swivel member is provided so that the motor is rotatable relative to the conduit from an aligned position, wherein the motor axis generally is aligned with the conduit axis, to an angularly displaced position, wherein the motor axis intersects the conduit axis at a selected angle.

29 Claims, 9 Drawing Sheets

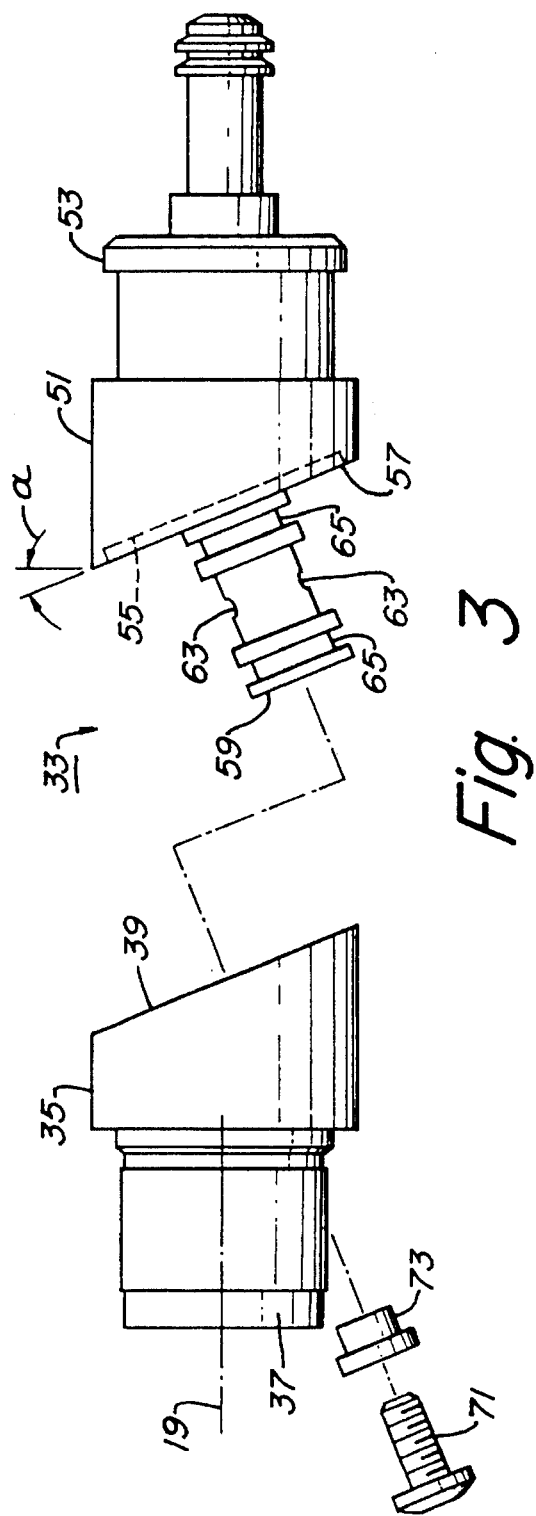
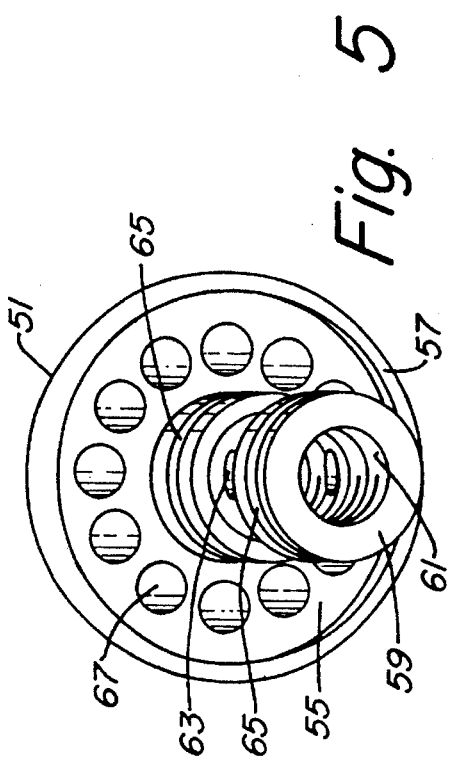
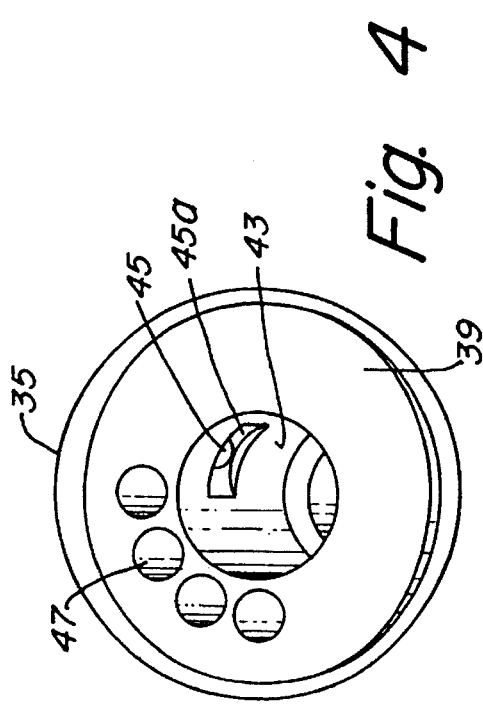
Fig. 3
Fig. 5
Fig. 4

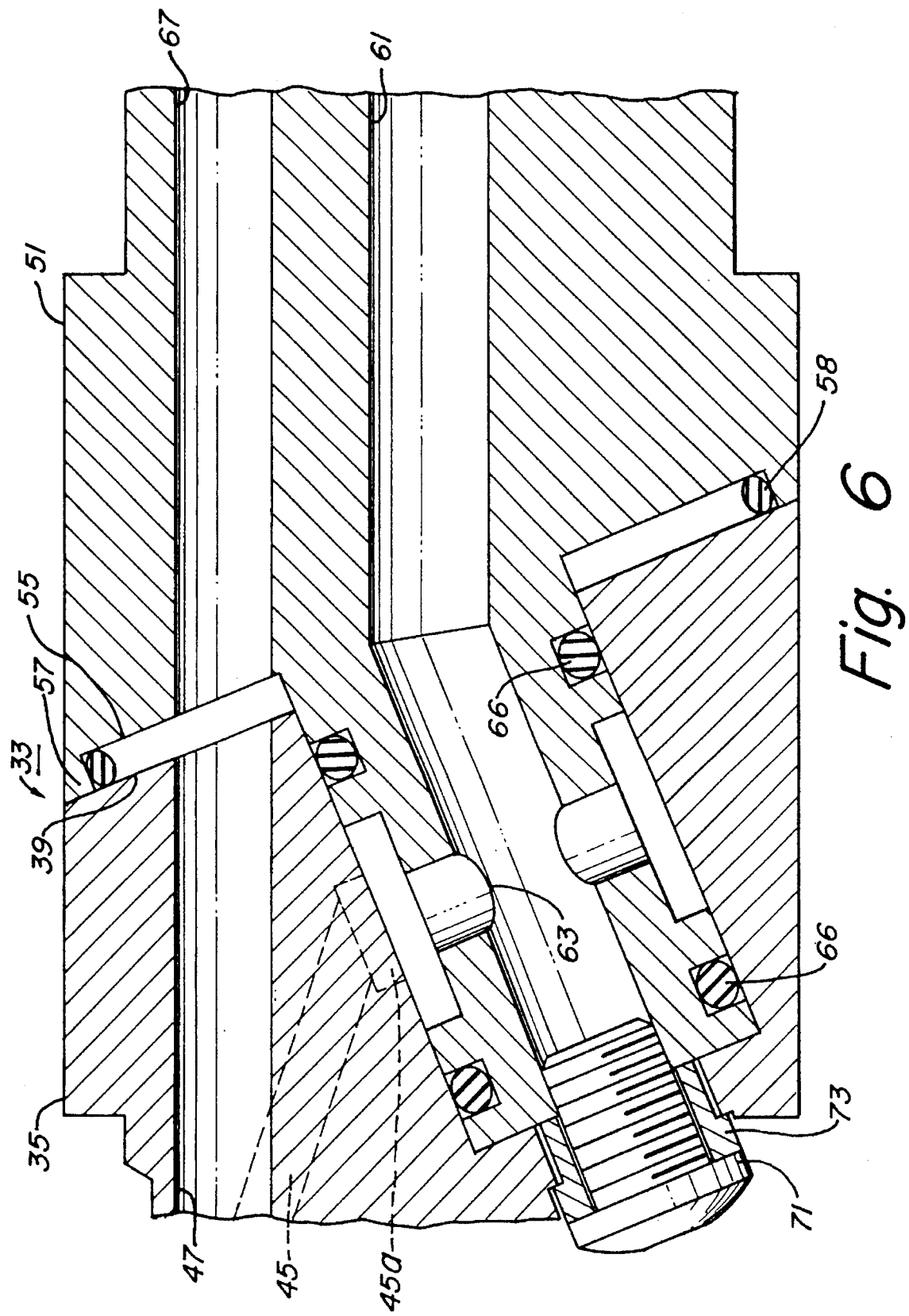

SURGICAL INSTRUMENT WITH SWIVEL MEMBER

CROSS-REFERENCE TO RELATED APPLICATIONS

This application is a continuation-in-part of application Ser. No. 07/958,229 filed Oct. 8, 1992, now U.S. Pat. No. 5,352,234.

BACKGROUND OF THE INVENTION

1. Field of the Invention

The present invention generally relates to surgical instruments for the dissection of bone or other tissue. More particularly, the present invention relates to a swivel apparatus for attaching a surgical instrument motor to a fluid conduit, the apparatus providing the ability to swivel the motor relative the fluid conduit.

2. Background Information

Surgical instruments employing fluid-powered motors to rotate cutting or dissection tools are conventional and well-known in the art. Such surgical tools are used in such delicate surgical operations as brain surgery and microsurgery. These surgical instruments must be capable of sanitary operation without contaminating an operating-room environment. Also, because of the delicate nature of surgery, the surgical instrument must be manipulated easily by the surgeon without causing undue fatigue, which could lead to disastrous surgical errors.

A number of surgical tools have hand pieces or cutting ends that are angularly displaced with respect to the fluid conduit, which supplies the fluid pressure necessary to power the motor, which in turn rotates a cutting or dissecting tool. The angularly displaced hand piece and dissecting tool provides an advantageous arrangement for manipulation of the surgical tool by the surgeon or user.

Such angled tools are disclosed, for example, in U.S. Pat. Nos. 1,677,337, Jul. 17, 1928 to Grove; 3,847,154, Nov. 12, 1974 to Nordin; 4,055,185, Oct. 25, 1977 to Waldron; 4,071,029, Jan. 31, 1978 to Richmond et al.; and 4,827,615, May 9, 1989 to Graham.

A drawback of these angled surgical tools is that they are permanently angularly displaced from the fluid conduit. This is a drawback for the user because at some stages of the surgery, the user may desire a "straight" surgical tool, and at other times the user may desire an angled surgical tool. With the prior-art surgical tools, a surgeon either must have one of each type available, or must interchange straight and angled hand pieces with a single fluid conduit. Having each type of surgical tool available can be quite cumbersome because each surgical tool requires its own fluid conduit, which can be quite inconvenient during the pressure and stress of surgery. Switching between each type of surgical tool, on a single fluid conduit, can be time-consuming when time frequently is of the essence.

A need exists to provide a surgical instrument, including a fluid-powered motor for rotating a dissecting tool, that is manipulated easily from an aligned position in which the motor axis and the fluid conduit axis are aligned, to an angularly displaced position in which the motor axis intersects the fluid conduit axis at a selected angle.

A need also exists to provide a surgical instrument as described above, wherein the motor is rotatably coupled to the conduit wherein the surgical instrument can be manipulated without twisting or kinking the fluid conduit.

SUMMARY OF THE INVENTION

It is a general object of the present invention to provide a surgical instrument for use in dissecting tissue that is capable of being manipulated from an aligned position to an angularly displaced position for improved manipulation of the surgical instrument by the user.

This and other objects are accomplished by providing a surgical instrument including a conduit, the conduit having a conduit axis defined through a terminal end thereof, and a fluid-powered motor for rotating a dissecting tool, the motor having a longitudinal motor axis. A swivel member is connected in fluid communication between the motor and the conduit. The swivel member comprises a motor portion including a motor face inclined at a selected angle from the motor axis, and a conduit portion including a conduit face arranged oppositely that of the motor face and formed to engage matingly with the motor face. A connection shaft extends from one of the motor face and the conduit face and is engaged rotatably with a connection receptacle formed in another of the motor face and the conduit face. The swivel member is provided so that the motor is rotatable relative to the conduit from an aligned position, wherein the motor axis generally is aligned with the conduit axis, to an angularly displaced position, wherein the motor axis intersects the conduit axis at a selected angle.

According to the preferred embodiment of the present invention, the means fastening the connection shaft in the receptacle is a plurality of ball members disposed in a ball race formed between the shaft and receptacle.

According to one embodiment of the present invention, the angular swivel means is provided with a detent means coupled between the connection shaft and connection receptacle to temporarily restrain the motor in either the aligned or angularly displaced positions.

According to another embodiment of the present invention, the conduit and motor faces are not inclined, but straight, thus providing a surgical instrument with a non-angular, straight swivel to permit the motor to rotate relative to the fluid conduit to avoid twisting and kinking of the conduit.

According to another embodiment of the present invention, both straight and angular swivels are provided between the motor and fluid conduit.

Other objects, features, and advantages of the present invention will be apparent to those skilled in the art with reference to the drawings and detailed description which follow.

DESCRIPTION OF THE DRAWINGS

FIG. 3 is an exploded elevation view of the swivel member of the surgical instrument of FIGS. 1 and 2.

FIG. 4 is an elevation end view of the conduit portion of the swivel member illustrated in FIG. 3.

FIG. 5 is an elevation view of the motor portion of the swivel member illustrated in FIG. 3.

FIG. 6 is a fragmentary, longitudinal section view of the assembled swivel member, illustrating the engagement of the various parts thereof.

DESCRIPTION OF THE PREFERRED EMBODIMENT

Figure 1:
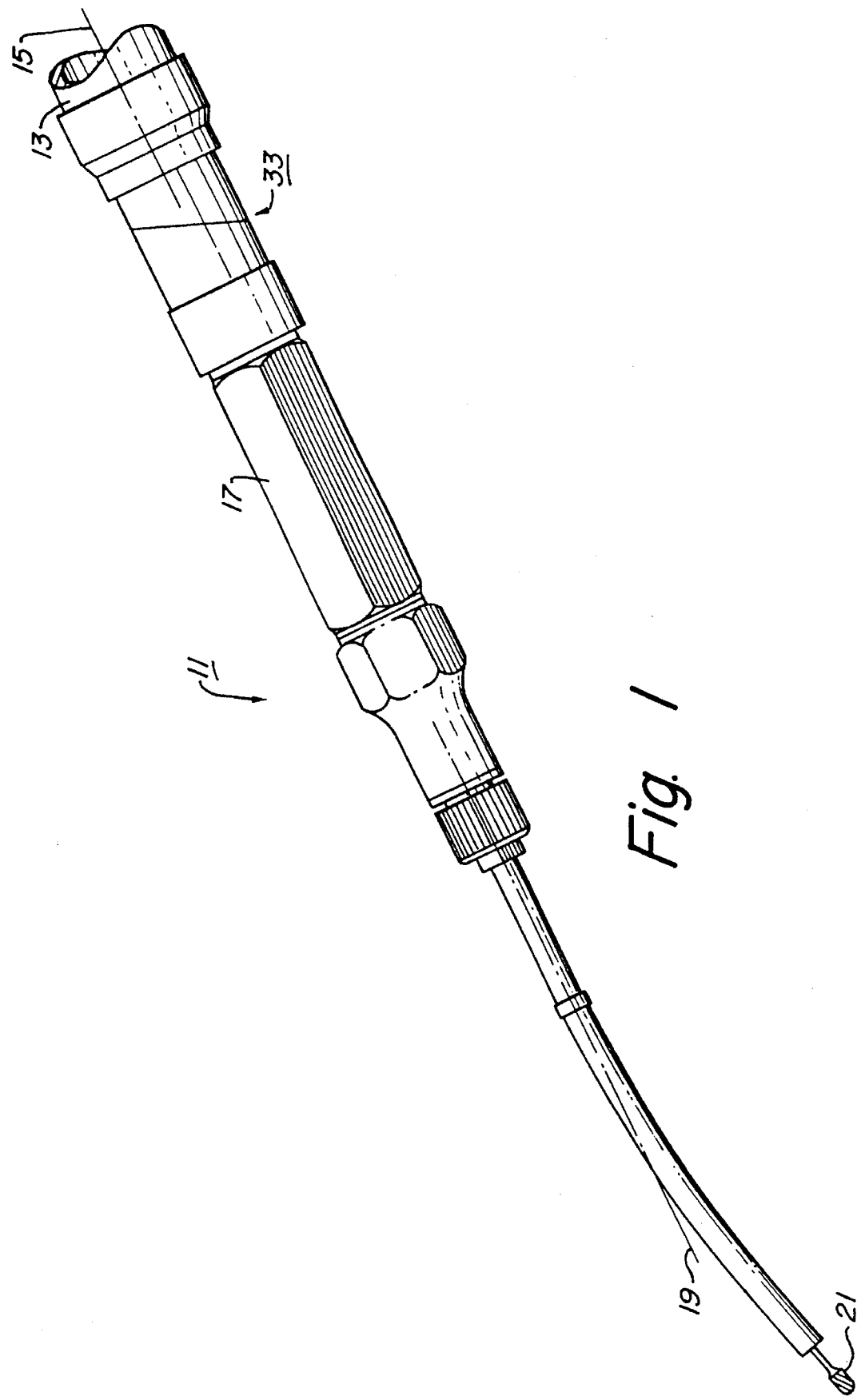
FIG. 1 is an elevation view of a surgical instrument according to the present invention shown in an aligned position.

Referring now to the Figures, and particularly to FIG. 1, the surgical instrument according to the present invention will be described. FIG. 1 illustrates, in elevation view, a surgical instrument 11 according to the present invention. Surgical instrument 11 comprises a fluid conduit 13 having a longitudinal conduit axis 15 defined at a terminal end thereof. Fluid conduit 13 is connected in fluid communication with a fluid-powered motor 17, which has a longitudinal motor axis 19. Motor 17 rotates a cutting or dissecting tool 21 in response to fluid pressure from fluid conduit 13. A swivel means or member 33 is connected in fluid communication between fluid conduit 13 and motor 17. FIG. 1 depicts surgical instrument 11 in an aligned position in which longitudinal conduit axis 15 and longitudinal motor axis 19 are substantially aligned.

Figure 2:
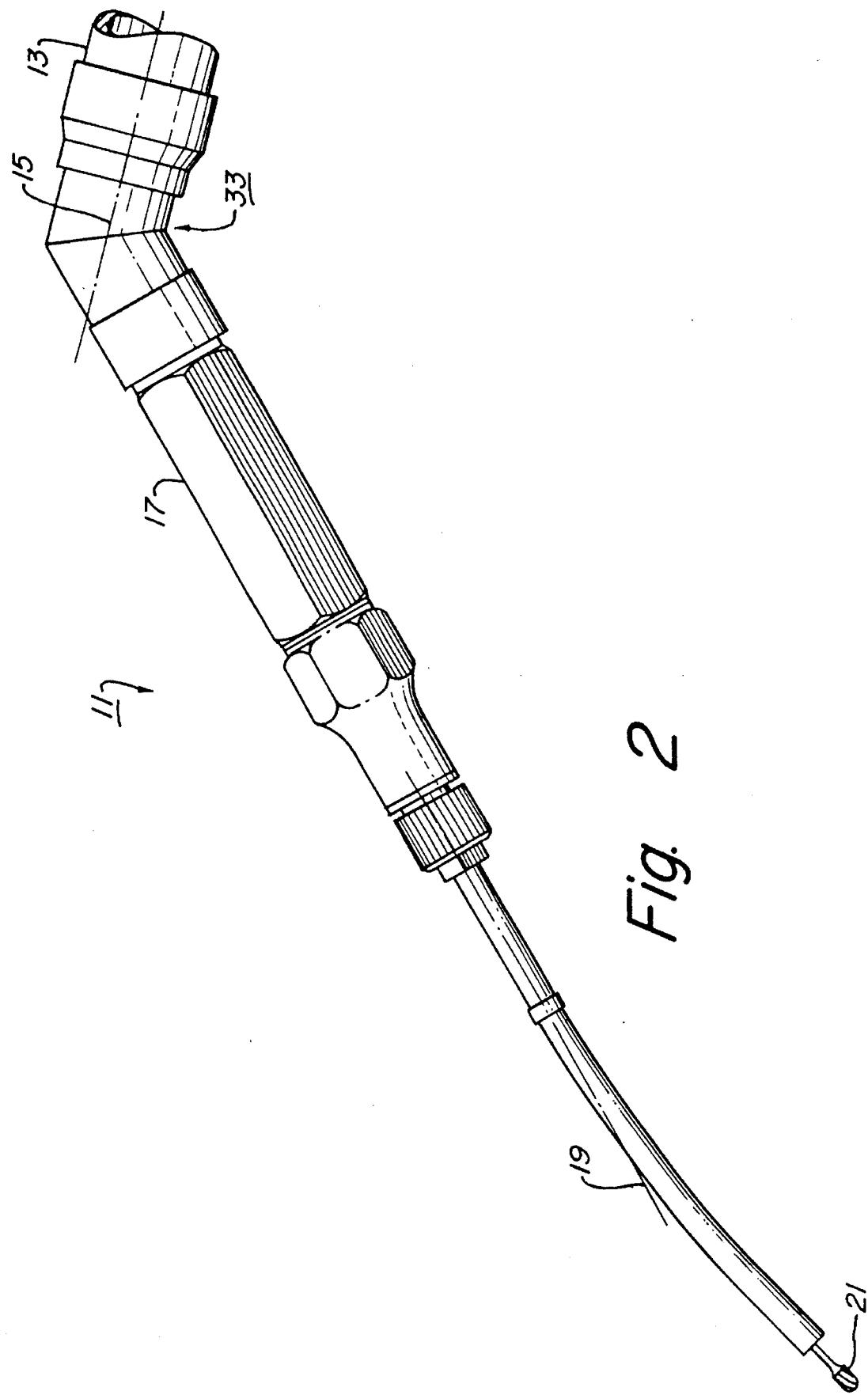
FIG. 2 is an elevation view of the surgical instrument according to the present invention shown in an angularly displaced position.

FIG. 2 depicts surgical instrument 11 of FIG. 1 in an angularly displaced position in which longitudinal conduit axis 15 and longitudinal motor axis 19 intersect at a selected angle. Preferably, the selected angle between longitudinal conduit axis 15 and longitudinal motor axis 19 is 45 degrees, measured as the acute angle included between axes 15, 19. Swivel means or member 33 permits manipulation of surgical tool 11 from the aligned position, illustrated in FIG. 1, to the angularly displaced position illustrated in FIG. 2.

Referring now to FIGS. 3 through 6, swivel member 33 comprises a motor portion 35 for connection in fluid communication to the motor (17 in FIGS. 1 and 2) at one end 37 thereof. An inclined motor face 39 is provided at an opposite end of motor portion 35. Inclined motor face 39 is inclined at a selected angle α, which is measured normally to longitudinal motor axis 19. Preferably, angle α is 22.5 degrees, which yields an ultimate angular displacement of 45 degrees.

Motor portion 35 is further provided with a connection receptacle 43 formed in motor face 39. Connection receptacle 43 is cylindrical and is normal to motor face 39. A motor fluid inlet passage 45 is formed in connection receptacle 43 for fluid communication with pair of fluid ports 63. Inlet passage 45 delivers air pressure to rotate motor 17. Inlet passage 45 terminates in a semi-annular recess 45a in receptacle 43. Motor portion 35 is further provided with a plurality of, in this case four, motor fluid exhaust passages 47. Exhaust passages 47 provide a return for the air delivered to motor 17.

Swivel member 33 also comprises a conduit portion 51 for connection in fluid communication at one end 53 thereof with fluid conduit (13 in FIGS. 1 and 2). Conduit portion 51 is further provided with a conduit face 55, which is arranged oppositely motor face 39, and is adapted to engage matingly with motor face 39. Conduit face 55 is further provided with conduit face lip 57, which cooperates with motor face 39 to define a receptacle for a sealing member 58 (FIG. 6).

A hollow, internally threaded connection shaft 59 extends from and normally to conduit face 55. Connection shaft 59 is adapted for mating engagement with connection receptacle 43 (FIG. 6) in motor portion 35. Connection shaft 59 is provided with a pair of fluid ports 63 extending through its sidewall for communication with fluid inlet recess 45a and passage 45 in motor portion 35. Connection shaft 59 is further provided with a pair of seal receptacles 65 for receiving seal members 66 for sealing engagement of connection shaft 59 with connection receptacle 43 of motor portion 35.

A conduit fluid inlet passage 61 (FIG. 6) is formed centrally through and coaxially with connection shaft 59 and conduit portion 51. A plurality of conduit fluid exhaust passages 67 are formed in conduit portion 51 and are circumferentially spaced about connection shaft 59, as illustrated in FIG. 5.

A fastening means 71, in this case a screw, is provided to secure connection shaft 59 of conduit portion 51 in the connection receptacle of motor portion 35, wherein motor face 39 and conduit face lip 57 are engaged rotatably and matingly. Fastener 71 is further provided with an anti-friction bushing 73 to insure smooth and free rotation of motor portion 35 relative to conduit portion 51.

FIG. 6 depicts, in fragmentary longitudinal section, assembled swivel member 33 and the mating rotatable engagement between motor portion 35 and conduit portion 51. As illustrated, connection shaft 59 of motor portion 51 is received by connection receptacle 43 of motor portion 35. Fluid inlet communication is established between fluid conduit 13 and motor 17 through conduit fluid inlet passage 61 in conduit portion 51, fluid ports 63, connection shaft 59, and motor fluid inlet passage 45. Connection shaft 59 is sealed against fluid leakage within connection receptacle 43 by seal members 66, in this case O-rings, fit in seal receptacles 65 of connection shaft 59.

Figure 7:
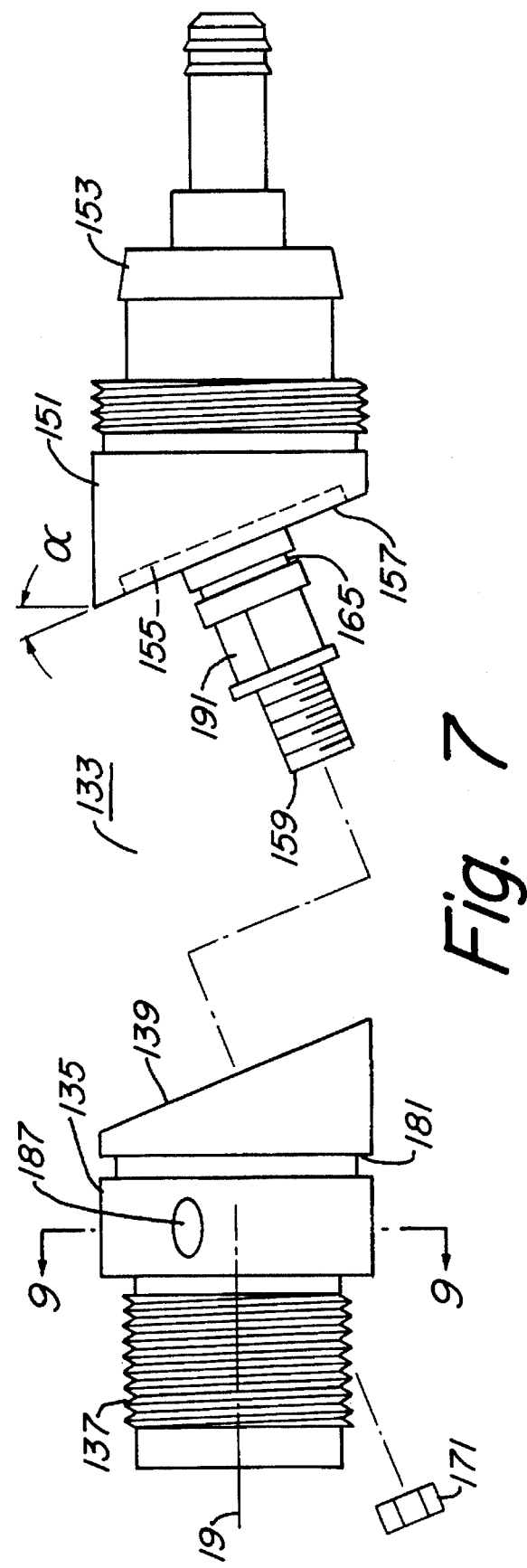
FIG. 7 is an exploded elevation view of a swivel member according to the present invention.
Figure 8:
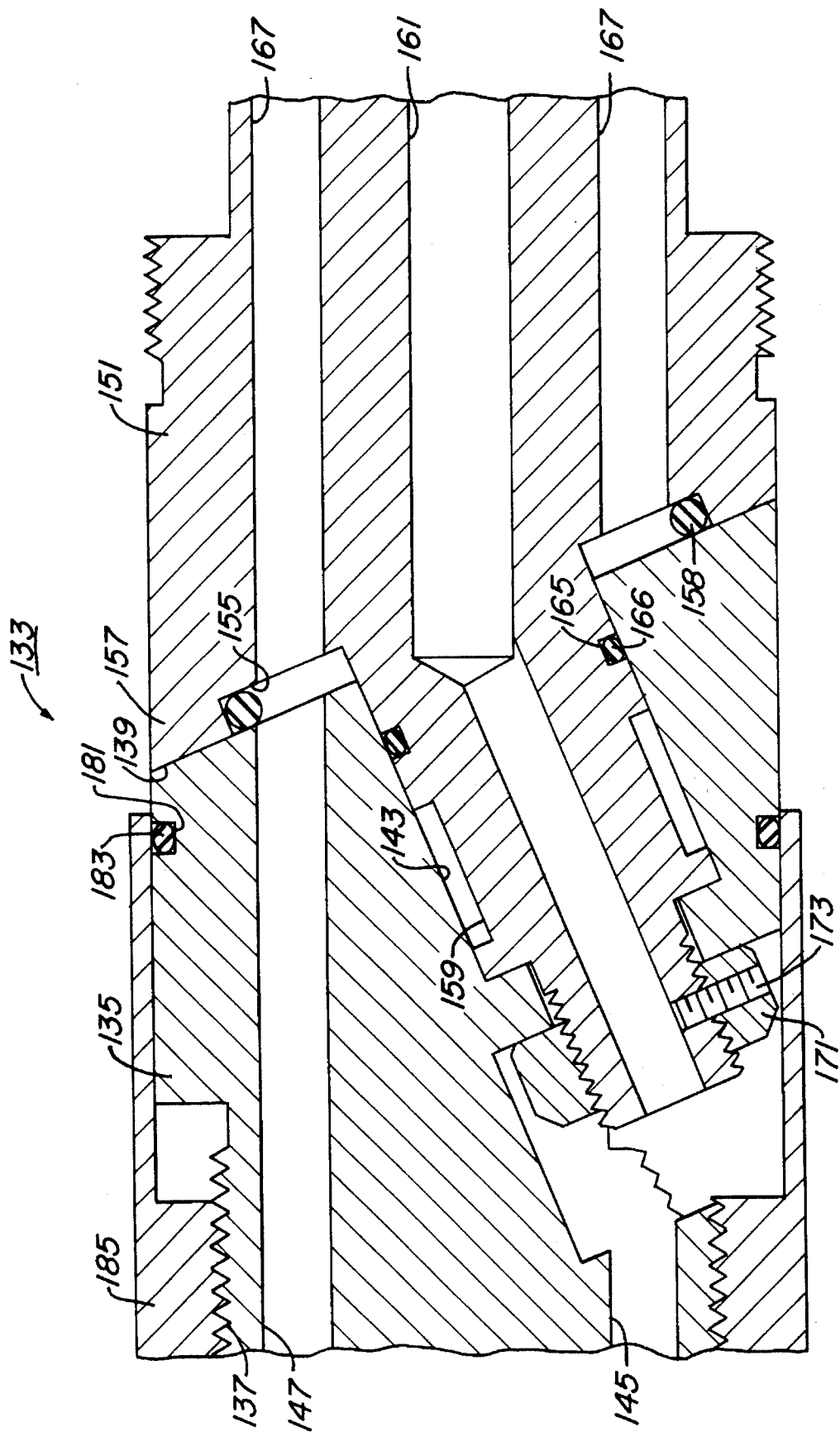
FIG. 8 is a fragmentary, longitudinal section view of the swivel member illustrated in FIG. 7.
Figure 9:
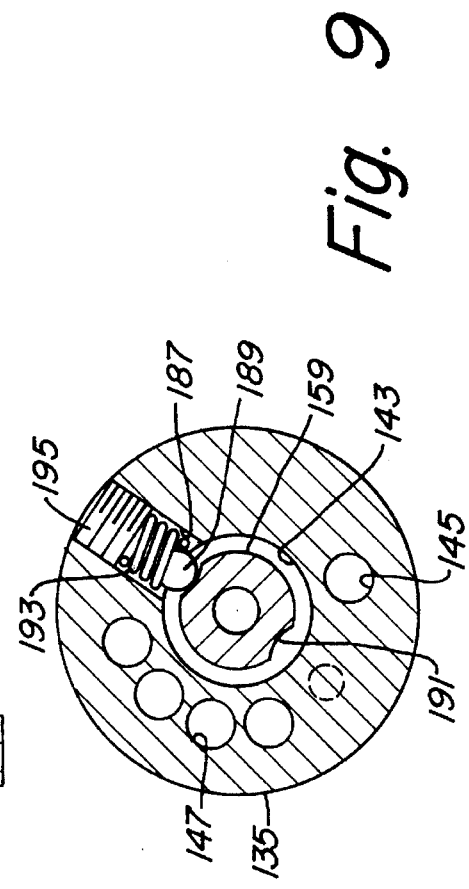
FIG. 9 is a cross-section view of a portion of the swivel member, taken along section line 9—9 of FIG. 7.

With reference now to FIGS. 7–9, another embodiment of a swivel member 133 according to the present invention is illustrated. FIG. 7 is an exploded elevation view of swivel member 133. FIG. 8 is a fragmentary, longitudinal section view of swivel member 133, as assembled. Swivel member 133 comprises a motor portion 135 for connection in fluid communication to the motor (17 in FIGS. 1 and 2) at one end 137 thereof. An inclined motor face 139 is provided at an opposite end of motor portion 135. Inclined motor face 139 is inclined at a selected angle α, which is measured normally to the longitudinal motor axis (19 in FIGS. 1 and 2). Preferably, angle α is 22.5 degrees, which yields an ultimate angular displacement of 45 degrees.

Motor portion 135 is further provided with a connection receptacle 143, which is cylindrical and normal to inclined motor face 139. A fluid inlet passage 145 is provided in fluid communication with connection receptacle 143 to deliver air pressure to rotate the motor (17 in FIG. 1). Motor portion 135 is further provided with a plurality of motor fluid exhaust passages 147, which provide a return for the air delivered to the motor (17 in FIG. 1), and are arranged similarly to those illustrated in FIG. 4.

Swivel member 133 also includes a conduit portion 155 for connection in fluid communication at one end 153 thereof with the fluid conduit (12 in FIGS. 1 and 2). Conduit portion 151 is further provided with a conduit face 155, which is arranged oppositely of motor face 139 and is adapted to engage matingly with motor face 139. Conduit face 155 is further provided with a conduit face lip 157, which cooperates with motor face 139 to define a receptacle for a sealing member 158.

A hollow, externally threaded connection shaft 159 extends from and normally to conduit face 155. Connection shaft 159 is adapted for mating engagement with connection receptacle 143 in motor portion 135. Connection shaft 159 is provided with a seal groove or receptacle 165 for receiving a seal member 166 for sealing engagement of connection shaft 159 with connection receptacle 143 of motor portion 135. A conduit fluid inlet passage 161 is formed centrally through conduit portion 151 and extends coaxially through connection shaft 159. A plurality of conduit fluid exhaust passages 167 are formed in conduit portion 151 and are circumferentially spaced about connection shaft 159 similar to those illustrated in FIG. 5.

A fastening means 171, in this case a nut, is provided to secure connection shaft 159 of conduit portion 151 in connection receptacle 143 of motor portion 135, wherein motor face 139 and conduit face lip 157 are engaged rotatably and matingly. Fastener 171 is further provided with a set screw 173 to prevent inadvertent disengagement with the threaded portion of connection shaft 159. A shroud member 185 is secured by threads to end 137 of motor portion 135 and extends over the cavity in which fastener 171 is received. A seal receptacle 181 and seal member 183 seal shroud 185 and motor portion 135 against fluid leakage therebetween and to establish fluid communication between inlet passage 161 in conduit portion 151 and inlet passage 145 in motor portion 135.

A detent receptacle 187 is formed in motor portion 135 and extends radially into connection receptacle 143. As shown in FIG. 9, which is a cross-section view of motor portion 135 taken along section line 9—9 of FIG. 7, detent receptacle 187 houses a detent mechanism including a spherical detent member 189, which engages detent recesses 191 on connection shaft 159. Detent member 189 is biased into engagement with detent recesses 191 by a coil spring 193, which is retained in detent receptacle 187 by a threaded plug 195. Detent recesses 191 on connection shaft 159 are spaced 180° apart and are located to correspond with the aligned and angularly displaced positions of swivel member 133 and surgical instrument 11 (as illustrated in FIGS. 1 and 2). This detent assembly thus temporarily secures swivel member 133 in either the aligned or angularly displaced positions.

Figure 10:
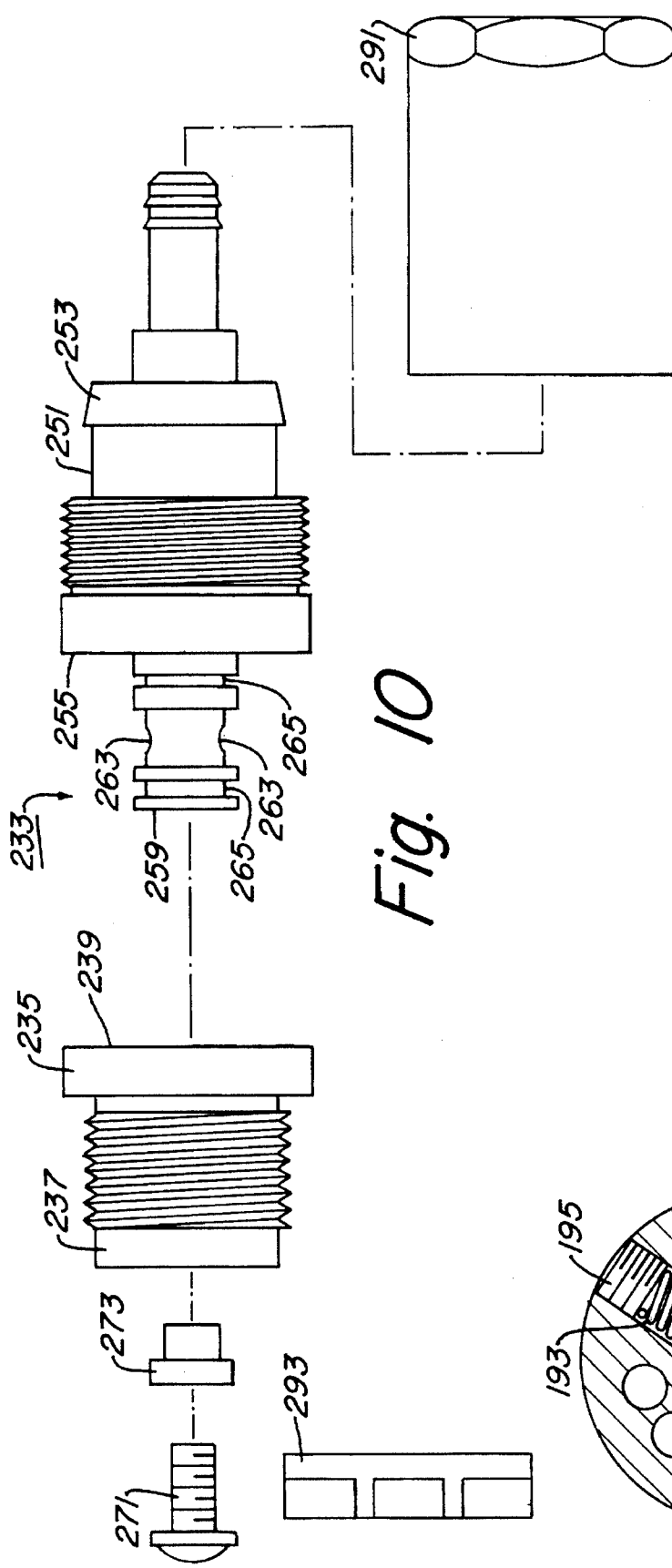
FIG. 10 is an exploded elevation view of a non-angular swivel according to the present invention.
Figure 11:
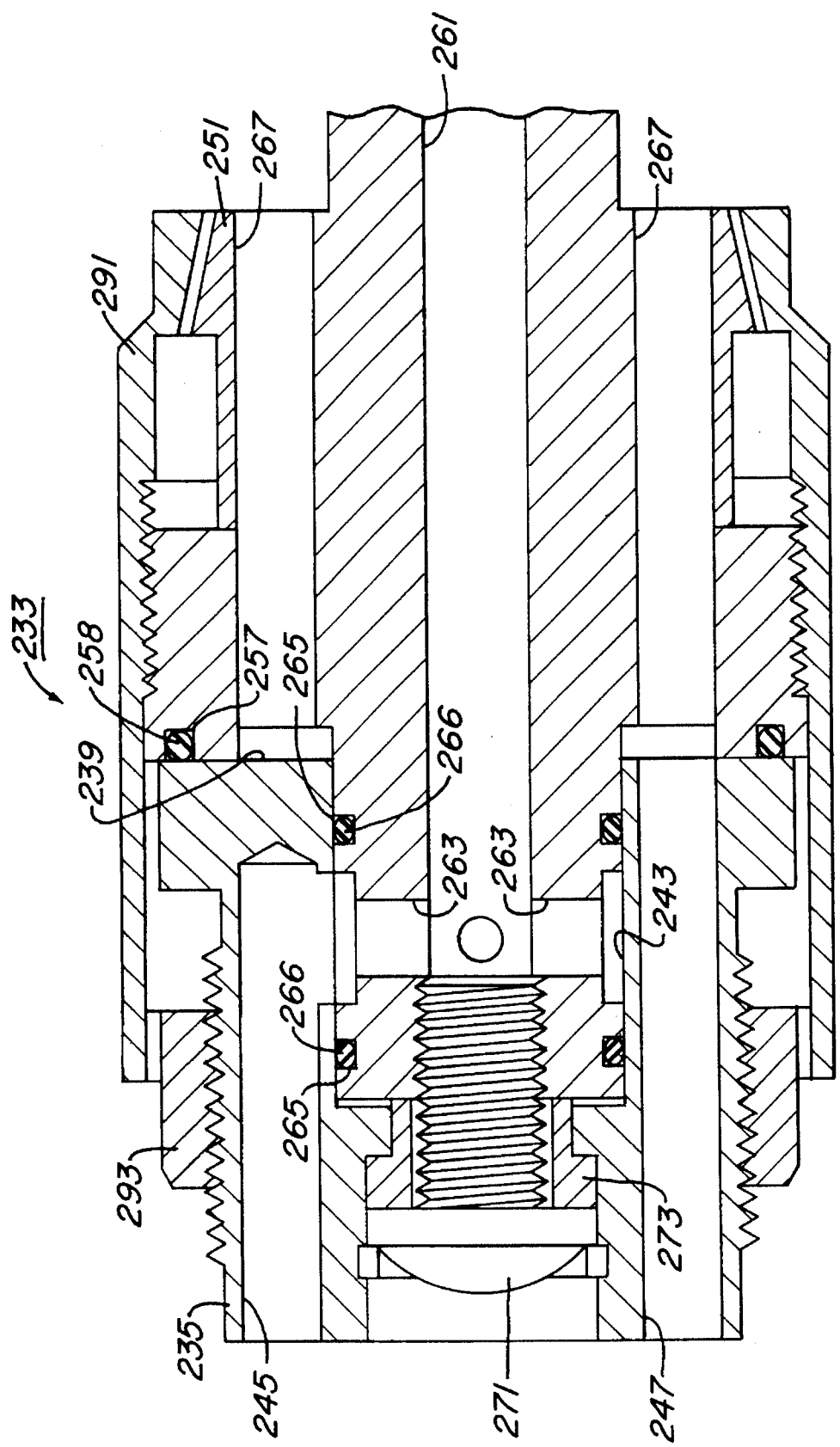
FIG. 11 is a fragmentary, longitudinal section view of the non-angular swivel of FIG. 10.

Referring now to FIGS. 10 and 11, yet another embodiment of a swivel member 233 according to the present invention is depicted. Non-angular swivel member 233 does not provide for angular displacement of the motor (17 in FIGS. 1 and 2) relative to the conduit (12 in FIGS. 1 and 2), but does provide for rotational movement of the motor relative to the conduit. FIG. 10 is an exploded elevation view of swivel member 233. FIG. 11 is a fragmentary, longitudinal section view of swivel member 233 as assembled. Swivel member 233 comprises a motor portion 235 for connection and fluid communication to the motor (17 in FIGS. 1 and 2) at one end 237 thereof. A motor face 239 is provided at an opposite end of motor portion 235 and is generally transverse to the longitudinal axis of the motor.

Motor portion 235 is further provided with a connection receptacle 243, which is cylindrical and normal to motor face 239. A fluid inlet passage 245 is provided in fluid communication with connection receptacle 243 to deliver air pressure to rotate the motor (17 in FIGS. 1 and 2). Motor portion 235 is further provided with a plurality of motor fluid exhaust passages 247, which provide a return for the air delivered to the motor (17 in FIGS. 1 and 2), and are arranged similarly to those illustrated in FIG. 4.

Swivel member 233 also includes a conduit portion 255 for connection and fluid communication at one end 253 thereof with the fluid conduit (12 in FIGS. 1 and 2). Conduit portion 251 is further provided with a conduit face 255, which is arranged generally oppositely a motor face 239 and is adapted to engage matingly with motor face 239. Conduit face 255 is further provided with a conduit seal recess 257, which cooperates with motor face 239 to define a receptacle for a sealing member 258, preferably an O-ring.

A hollow connection shaft 259 extends from and normally to conduit face 255. Connection shaft 259 is adapted for mating engagement with connection receptacle 243 in motor portion 235. Connection shaft 259 is provided with a pair of seal grooves or receptacles 265 for receiving a pair of seal members 266, preferably O-rings, for sealing engagement of connection shaft 259 with connection receptacle 243 of motor portion 235. A conduit fluid inlet passage is formed centrally through conduit portion 251 and extends coaxially through connection shaft 259. A pair of fluid ports 263 are formed in connection shaft 259 to establish fluid communication with fluid inlet passage 245 to deliver fluid pressure to the motor (17 in FIGS. 1 and 2). A plurality of conduit fluid exhaust passages 267 are formed in conduit portion 251 and are circumferentially spaced about connection shaft 259 similar to those illustrated in FIG. 5. A fastening means 271, in this case a screw, is provided to secure connection shaft 259 of conduit portion 251 in connection receptacle 243 of motor portion 235, wherein motor face 239 and conduit face 257 are engaged rotatably and matingly. Fastener 271 is further provided with an anti-friction bushing 273 to insure smooth and free rotation of motor portion 235 relative to conduit portion 251. A shroud member 291 is secured to threads on the exterior of conduit portion 251 and extends over motor portion 235. The rear portion of shroud 291 serves to secure a portion of fluid conduit 13 (FIG. 1) to swivel 233. A motor lock nut 293 is carried by external threads on motor portion 235 to assist in securing motor portion 235 to the motor (17 in FIGS. 1 and 2).

Fluid exhaust communication is established between motor 17 (FIG. 1) and fluid conduit 13 (FIG. 1) by motor fluid exhaust passages 47, 147, 247 which mate with conduit fluid exhaust passages 67, 167, 267 at the interface between motor face 39, 139, 239 and mating conduit face 55, 155, 255. Motor face 39, 139, 239 and conduit face lip 57, 157, 257 cooperate to define a seal receptacle for receiving face seal member 58, 158, 258 in this case, an O-ring, for sealing motor face 39, 139, 239 and conduit mating face 55, 155, 255 against fluid leakage therebetween.

As is illustrated, not all of the plurality of conduit fluid exhaust passages 67, 167, 267 will align with mating motor fluid exhaust passages 47, 147, 247. However, a sufficient number of motor fluid exhaust passages 47, 147, 247 will align with conduit fluid exhaust passages 67, 167, 267 to permit exhaust of fluid from motor 17 (FIG. 1), if swivel member 33, 133, 233 is constructed as illustrated in FIGS. 4–11. Rotating conduit portion 51, 151, 251 relative to motor portion 35, 135, 235 causes different alignment of exhaust passage 47, 147, 247 with exhaust passages 67, 167, 267.

Figure 13:
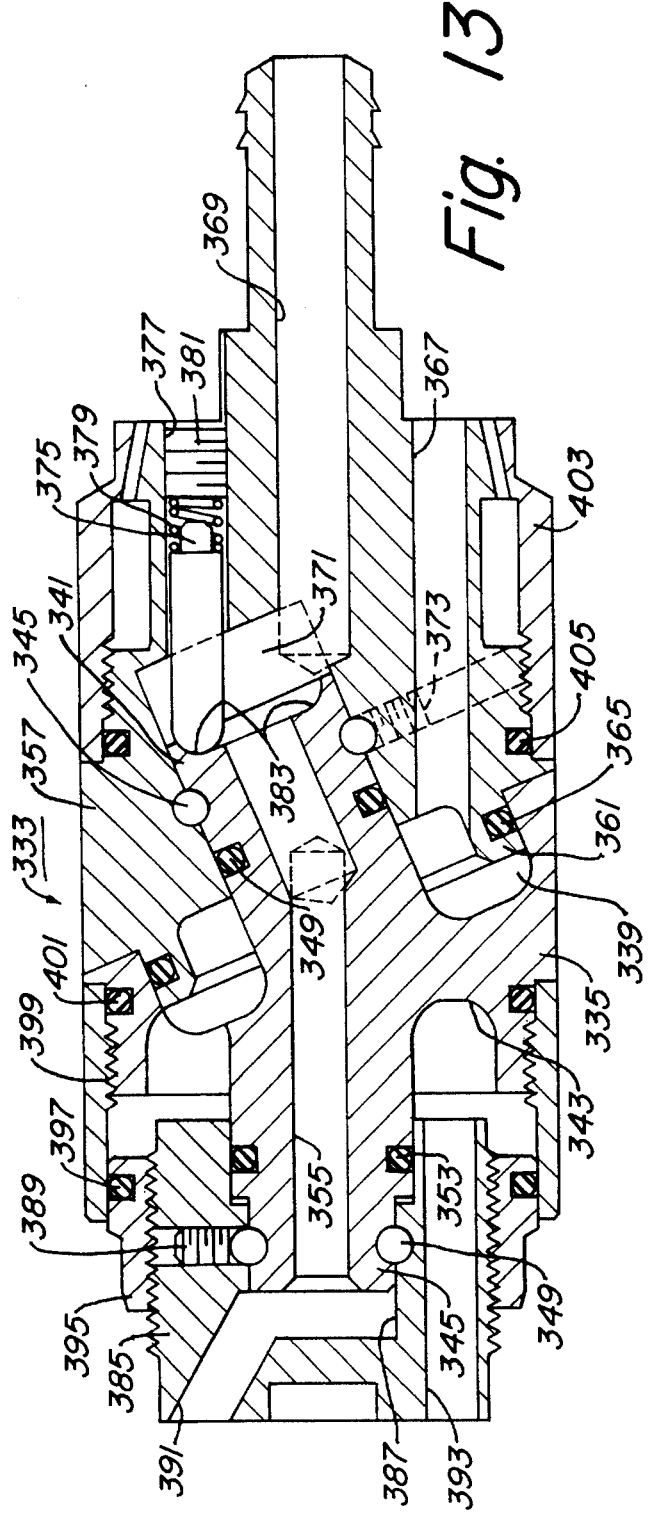
FIG. 13 is a longitudinal section view of the combination swivel of FIG. 12.
Figure 12:
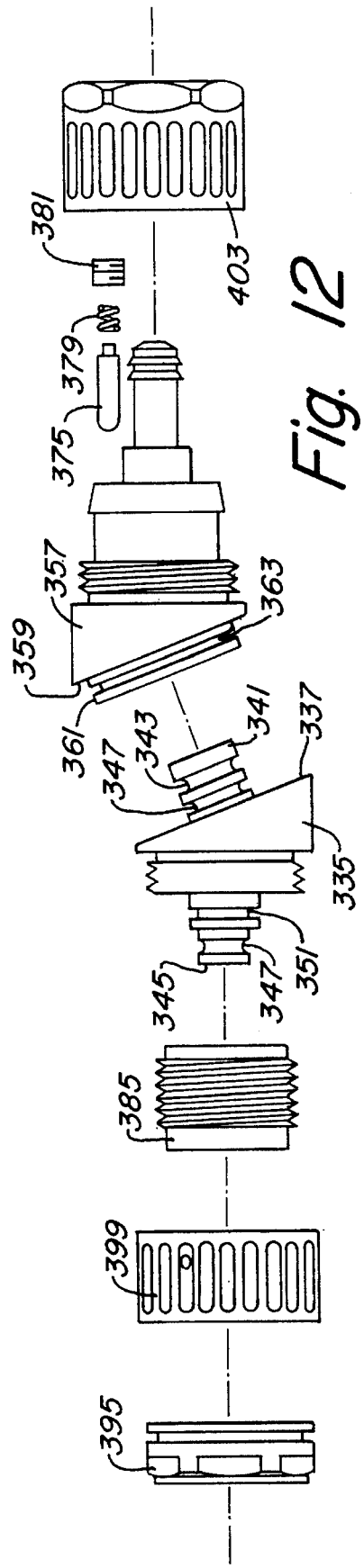
FIG. 12 is an exploded view of a combination angular and non-angular swivel according to the present invention.

FIGS. 12 and 13 are exploded elevation and assembled, longitudinal section views, respectively, of another swivel member 333 according to the preferred embodiment of the present invention. As will be seen, swivel member 333 incorporates the features of the angular swivels described in FIGS. 1–8 with the non-angular or straight swivel described in FIGS. 10–11. Swivel member 333 includes a central swivel member 335, which includes an inclined conduit face 337, preferably inclined at an angle of 22.5 degrees as described with reference to FIG. 3. A generally circular recess 339 is formed in conduit inclined face 337.

A hollow, cylindrical conduit connection shaft 341 extends from central swivel member 335 and generally normal to inclined conduit face 337. Connection shaft 341 includes a portion of a ball race 344 for engagement with a plurality of ball members 345. A seal recess 347 is also provided in conduit connection shaft 341 to accommodate a seal member 349, preferably an O-ring. A generally circular recess 343 is formed on an opposite end of central swivel member 335 and intersects generally circular recess 339 formed in inclined conduit face 337 to provide fluid communication from one end of central swivel member 335 to the other.

A motor connection shaft 346 extends from a generally opposite end of central swivel member 335 and includes a ball race 347 for engagement with ball members 350 and a seal recess 351 to accommodate a seal member 353, preferably an O-ring. A fluid inlet passage 355 extends through central swivel member 335 and coaxially through connection shafts 341, 345.

A conduit portion 357 has one end adapted for connection to fluid conduit 13 (FIG. 1). A mating conduit inclined face 359 is formed at the other end of conduit portion 357 for mating engagement with inclined conduit face 337 of central swivel portion member 335. A shoulder 361 projects from conduit portion 357 beyond mating inclined conduit face 359 and includes a seal receptacle 363 to accommodate a seal member 365, preferably an O-ring. Shoulder 361 and seal member 365 engage circular recess 339 in inclined conduit face 337 of central swivel member 335 to seal inclined faces 337, 359. A cylindrical conduit connection receptacle 371 is formed in conduit portion 357 substantially normal to mating circuit inclined face 359.

A plurality of fluid exhaust passages 367 are formed in conduit portion 357 about the periphery of connection receptacle 371, substantially as is illustrated in FIG. 5. A fluid inlet passage 369 extends through the center of conduit portion 357 and terminates in fluid communication with conduit connection receptacle 371, which receives conduit connection shaft 341 of central swivel member 335 in rotatable engagement. As illustrated in FIG. 13, conduit connection shaft 341 is rotatably received in conduit connection and secured therein by a fastener in the form of a plurality of ball elements 345 captured in a ball race 344 formed between conduit connection shaft 341 and connection receptacle 371. Balls 345 are loaded into ball race 343 through a ball-loading passage and retained there by a threaded plug 373. Seal member 349 seals the connection against fluid leakage.

An elongate detent member 375 is disposed in a detent passage 377 and biased by a coil spring 379 and a threaded plug 381 into engagement with one of a pair of detent recesses 383 in the end of conduit connection shaft 341. This detent means serves to releasably secure motor 11 in either the angularly displaced or aligned positions illustrated in FIGS. 1 and 2.

A motor portion 385 has a cylindrical motor connection receptacle 387 formed therein to rotatably receive motor connection shaft 346. Motor connection shaft 346 is secured in motor connection receptacle 387 by engagement between a plurality of ball members 350 in a ball race 347 formed between motor connection shaft 346 and motor connection receptacle 387. Ball members 350 are loaded through a ball-loading passage and retained there by a threaded plug 389. Seal member 353 seals the connection against fluid leakage.

A motor fluid inlet passage 391 is in fluid communication at one end with motor 17 (FIG. 1) and at another end with motor connection receptacle 387 and thus is in fluid communication with motor fluid inlet passage 355 in central swivel member 335. A plurality of fluid exhaust passages 393, arranged substantially as shown in FIG. 4, are disposed about the periphery of motor connection shaft 347 and are in fluid communication, through circular recesses 339, 343 in central swivel member 335, with fluid exhaust passages 367 in conduit portion 357.

A motor lock nut 395 is secured by threads to motor portion 385 and carries a seal member 397, preferably an O-ring, for engagement with a motor shroud 399 secured by threads to central swivel member 335. A seal member 401, preferably an O-ring, cooperates with motor shroud 399, seal member 397, and motor lock nut 395 to seal the connection between motor portions 385 and central swivel member 335 against fluid leakage from fluid exhaust conduits 393. A conduit shroud 403 is secured by threads to conduit portion 357, and, cooperating with seal member 405, secures and seals a portion of fluid conduit 13 to a conduit portion 357.

In this combination swivel embodiment, fluid is delivered to motor 17 from conduit 11 through fluid inlet passages 369, 355, 391, and fluid is exhausted from motor 17 through fluid exhaust passages 393, circular recesses 339, 343, and fluid exhaust passages 367. Ball members 345, 350 and races 344, 347 serve as a fastening means to secure central swivel member 335 to conduit portion 357 and motor portion 385 and facilitate rotation therebetween. Similar construction could be employed in the angular swivels of FIGS. 1–9 and the non-angular or straight swivels of FIGS. 10 and 11.

With reference to FIGS. 1 through 13, the operation of surgical instrument 11 according to the present invention will be described. Surgical instrument 11, including fluid conduit 13, motor 17, dissection tool 21, and swivel member 33, 133, 233, 333 is assembled and connected in fluid communication with a fluid pressure source (not shown), which is typically an operating room's compressed air supply.

Surgical operations, typically dissection of bone or other tissue, then are commenced using surgical instrument 11. The user or surgeon may desire that surgical instrument 11 be configured initially in the aligned position, in which motor longitudinal axis 19 is aligned with and substantially coaxial with longitudinal fluid conduit axis 15. Fluid pressure then is supplied from the fluid pressure source (not shown), through conduit 17 and swivel member 33, 133, 233, 333, to motor 17, which rotates dissection tool 21 for dissection of tissue. Fluid pressure is exhausted through swivel member 33, 133, 233, 333 and fluid conduit 13.

After the initial dissection operation is accomplished, the user or surgeon may desire to rotate motor 17 relative to fluid conduit 13 so that surgical instrument 11 is in an angularly displaced position, in which motor axis 19 intersects conduit axis 15 at a selected angle. The angularly displaced position of surgical instrument 11 is desirable to permit more careful and minute manipulation of dissection tool 21 after the initial dissection is accomplished. The angularly displaced position is achieved by rotating motor 17 relative to fluid conduit 13. Angular swivel 33, 133, 333 causes angular displacement of motor 17 relative to conduit 13.

In the angularly displaced position, pressurized fluid is delivered from the fluid pressure source (not shown) to motor 17 through swivel member 33, 133, 333. Motor 17 rotates dissecting tool 21 for dissection operation. Fluid pressure is exhausted from motor 17 through swivel 33, 133, 333 and conduit 13. Therefore, fluid inlet and exhaust communication between motor 17 and fluid conduit 13 exists at all times, regardless of the angular displacement of the motor 17 from conduit 13. In subsequent operations, motor 17 may be rotated relative to conduit 13 from the aligned position to the angularly displaced position, and vice-versa, any number of times.

Non-angular swivel member 233 operates similarly to angular swivels 33, 133, but because motor and conduit faces 239, 255 are not inclined, no angular displacement of motor 17 relative to fluid conduit 13 occurs. Combination swivel 333 combines the features of angular swivel member 33, 133, and non-angular swivel member 233 and possesses the advantages of both.

The surgical instrument according to the present invention has a number of advantages. A principal advantage of the present invention is that the motor may be rotated with respect to the fluid conduit from an aligned position to an angularly displaced position. This advantage obviates the necessity of interchanging straight and angled surgical instruments on a single fluid conduit. This advantage also obviates the need to have straight and angled surgical instruments connected to individual fluid conduits.

Provision of a surgical instrument with the ability to swivel from an aligned position to an angularly displaced position permits the user of the instrument to switch quickly and easily to an instrument configuration that is most appropriate for the operation being undertaken. Such flexibility of configuration eliminates fatigue and speeds surgical operations.

Provision of a surgical instrument with the ability to permit the motor to rotate relative to the conduit, with or without angular displacement, allows the user to manipulate the instrument without inconvenient twisting and kinking of the fluid conduit.

The present invention has been described with reference to a preferred embodiment thereof. Those skilled in the art will recognize that the present invention is susceptible to variations and modifications without departing from the scope thereof.

I claim:

1. In a surgical instrument for dissecting tissue, the surgical instrument including a conduit having a conduit axis defined through a terminal end thereof, and a fluid powered motor for rotating a dissecting tool, the motor having a longitudinal motor axis, the improvement comprising:

connection means for rotatably connecting the motor to the conduit and including swivel means for swiveling the motor relative to the conduit from an aligned position, in which the motor axis is aligned with the conduit axis, to an angularly displaced position, in which the motor axis intersects the conduit axis at a selected included angle, the swivel means including:
a motor portion in fluid communication with the motor;
a conduit portion in fluid communication with the conduit;
a connection shaft extending from one of the portions;
a connection receptacle formed in the other of the portions, the connection receptacle formed to receive the connection shaft in rotatable engagement; and
fastener means for securing the connection shaft in rotatable engagement with the receptacle cavity; and
detent means for releasably securing the motor in each of the aligned and angularly displaced positions.

2. The surgical instrument according to claim 1 wherein the swivel means further comprises:
a motor inclined face on the motor portion; and
an oppositely facing conduit inclined face on the conduit portion formed to sealingly engage the motor inclined face.

3. The surgical instrument according to claim 1 further comprising means for sealing the connection means against fluid leakage therefrom.

4. The surgical instrument according to claim 1 further comprising:
inlet passage means extending through the connection means for delivery of pressurized fluid to the motor; and
exhaust passage means extending through the connection means for exhausting pressurized fluid from the motor.

5. The surgical instrument according to claim 1 wherein the detent means further comprises:
a detent member biased into extension into the receptacle cavity and into engagement with the connection shaft; and
a pair of detent surfaces on the connection shaft, one of the detent surfaces registering with the detent member in the aligned position, another of the detent surfaces registering with the detent member in the angularly displaced position.

6. In a surgical instrument for dissecting tissue, the surgical instrument including a conduit having a conduit axis defined through a terminal end thereof, and a fluid-powered motor for rotating a dissecting tool, the motor having a longitudinal motor axis, the improvement comprising:
a motor portion connected in fluid communication with the motor, the motor portion including a motor face inclined at a selected angle from the motor axis;
a conduit portion connected in fluid communication with the conduit, the conduit portion having a conduit face arranged oppositely that of the motor face, the conduit face formed to rotatably engage with the motor face;
a connection receptacle formed in one of the faces;
a connection shaft extending from the other of the faces into rotatable engagement with the connection receptacle;
a motor inlet flow passage formed in the motor portion, the motor inlet flow passage being in communication with the motor at one end and with a fastener receptacle at the other end;
a conduit inlet flow passage formed in the conduit portion and extending through the connection shaft and into the fastener receptacle;
fastening means disposed in the fastener receptacle and securing the connection shaft in the connection receptacle, wherein the motor and motor portion are rotatable relative to the conduit and conduit portion from an aligned position, in which the motor axis generally is aligned with the conduit axis, to an angularly displaced position, in which in which the motor axis intersects the conduit axis at a selected angle; and seal means for preventing escape of fluid from the fastener receptacle, wherein the motor inlet flow passage is in fluid communication with the conduit inlet flow passage regardless of the angular position of the conduit portion relative to the motor portion.

7. The surgical instrument according to claim 6 further comprising detent means for releasably securing the motor in each of the aligned and angularly displaced positions.

8. The surgical instrument according to claim 6 further comprising:
 a plurality of motor exhaust flow passages formed in the motor portion, each having an end terminating at the motor face;
 a plurality of mating conduit exhaust flow passages formed in the conduit portion, each having an end terminating at the conduit face, wherein at least one of the motor exhaust flow passages communicates with at least one conduit exhaust flow passages regardless of the angular position of the conduit portion relative to the motor portion; and
 seal means for sealing the faces to each other against fluid leakage.

9. The surgical instrument according to claim 6 further comprising a face seal member disposed between the motor face and the conduit face.

10. The surgical instrument according to claim 6 further comprising at least one connection seal member disposed between the connection shaft and the connection receptacle.

11. The surgical instrument according to claim 6 wherein the motor face is inclined at an angle of substantially 22.5 degrees, and the selected angle of the angularly displaced position is substantially 45 degrees.

12. The surgical instrument according to claim 6 wherein the motor inlet passage is parallel to and offset from the motor axis.

13. The surgical instrument according to claim 6 further comprising:
 a detent member biased into extension into the receptacle cavity and into engagement with the connection shaft; and
 a pair of detent surfaces on the connection shaft, one of the detent surfaces registering with the detent member in the aligned position, another of the detent surfaces registering with the detent member in the angularly displaced position.

14. The surgical instrument according to claim 6 wherein the connection shaft is externally threaded and the fastening means is a nut.

15. A surgical instrument for dissecting tissue, the surgical instrument comprising, in combination:
 a motor responsive to fluid pressure to rotate a dissecting tool having a cutting head, the motor including a longitudinal motor axis;
 a conduit connected in fluid communication to the motor to provide fluid pressure to the motor from a fluid pressure source, the conduit including a longitudinal conduit axis defined at a terminal end thereof; and
 a swivel to permit the motor to swivel from an aligned position, in which the motor axis is substantially aligned with the conduit axis, to an angularly displaced position, in which the motor axis intersects the conduit axis at a selected angle, the swivel including:
  a motor portion connected in fluid communication with the motor, the motor portion including a motor face inclined at a selected angle from the motor axis;
  a conduit portion connected in fluid communication with the conduit, the conduit portion having a conduit face arranged oppositely that of the motor face, the conduit face formed to matingly engage with the motor face;
  a connection receptacle formed in one of the faces;
  a connection shaft extending from the other of the faces, into rotatable engagement with the connection receptacle;
  a first inlet flow passage formed in one of the portions extending through and coaxially with the connection shaft;
  a second inlet flow passage formed in the other portion and terminating in the connection receptacle so that fluid will flow through the first to the second inlet flow passage to supply fluid pressure to the motor regardless of the angular position of the conduit portion relative to the motor portion;
  a plurality of motor exhaust passages formed in the motor portion and terminating at the motor face;
  a plurality of mating conduit exhaust passages formed in the conduit portion and terminating at the conduit face, wherein at least one mating conduit exhaust passage mates in fluid communication with at least one of the motor exhaust passages;
  a face seal member sealingly engaged between the motor face and the mating conduit face and surrounding the ends of the exhaust flow passage;
  at least one connection seal member engaged between the connection shaft and the connection receptacle;
  a detent member biased into extension into the receptacle cavity and into engagement with the connection shaft; and
  a pair of detent surfaces on the connection shaft, one of the detent surfaces registering with the detent member in the aligned position, another of the detent surfaces registering with the detent member in the angularly displaced position.

16. The surgical instrument according to claim 15 wherein the connection shaft is externally threaded and is secured in the connection receptacle by a nut.

17. In a surgical instrument for dissecting tissue, the surgical instrument including a conduit having a conduit axis defined through a terminal end thereof, and a fluid powered motor for rotating a dissecting tool, the improvement comprising:
 connection means for rotatably connecting the motor to the conduit and including:
  a motor portion in fluid communication with the motor;
  a conduit portion in fluid communication with the conduit;
  a connection shaft extending from one of the portions;
  a connection receptacle formed in the other of the portions, the connection receptacle formed to receive the connection shaft in rotatable engagement;
  fastener means for securing the connection shaft in rotatable engagement with the connection receptacle;
  seal means disposed between the motor and conduit portions to seal against fluid leakage from the connection means;
  inlet passage means extending through the connection means for delivery pressurized fluid to the motor; and
  exhaust passage means extending through the connection means for exhausting pressurized fluid from the motor.

18. In a surgical instrument for dissecting tissue, the surgical instrument including a conduit having a conduit axis defined through a terminal end thereof, and a fluid-powered motor for rotating a dissecting tool, the improvement comprising:

a motor portion connected in fluid communication with the motor, the motor portion including a motor face perpendicular to the motor axis;

a conduit portion connected in fluid communication with the conduit, the conduit portion having a conduit face arranged oppositely that of the motor face, the conduit face formed to rotatably engage with the motor face;

a connection receptacle formed in one of the faces;

a connection shaft extending from the other of the faces into rotatable engagement with the connection receptacle, wherein the motor and motor portion are rotatable relative to the conduit a motor inlet flow passage formed in the motor portion;

a conduit inlet flow passage formed in the conduit portion;

communication means for communicating the motor inlet flow passage with the conduit inlet flow passage regardless of the angular position of the conduit portion relative to the motor portion;

a plurality of motor exhaust flow passages formed in the motor portion, each having an end terminating at the motor face;

a plurality of mating conduit exhaust flow passages formed in the conduit portion, each having an end terminating at the conduit face, wherein at least one of the motor exhaust flow passages communicates with at least one conduit exhaust flow passages regardless of the angular position of the conduit portion relative to the motor portion; and seal means for sealing the motor and conduit portions to each other against fluid leakage.

19. The surgical instrument according to claim 18 further comprising a face seal member disposed between the motor face and the conduit face.

20. The surgical instrument according to claim 18 further comprising at least one connection seal member disposed between the connection shaft and the connection receptacle.

21. In a surgical instrument for dissecting tissue, the surgical instrument including a conduit having a conduit axis defined through a terminal end thereof, and a fluid powered motor for rotating a dissecting tool, the motor having a longitudinal motor axis, the improvement comprising:

an angular swivel connecting the motor and fluid conduit for swiveling the motor relative to the conduit from an aligned position, in which the motor axis is aligned with the conduit axis, to an angularly displaced position, in which the motor axis intersects the conduit axis at a selected angle; and a second connection between the motor and conduit that permits the motor to rotate freely relative to the conduit.

22. The surgical instrument according to claim 21 wherein the angular swivel comprises:

a central swivel portion in fluid communication with the motor;

a conduit portion in fluid communication with the fluid conduit;

a conduit connection shaft extending from the central swivel portion;

a conduit connection receptacle formed in the conduit portion to receive the conduit connection shaft in rotatable engagement, wherein the motor is in fluid communication with the conduit.

23. The surgical instrument according to claim 22 wherein the second connection comprises:

a motor portion in fluid communication with the motor;

a motor connection shaft extending from the central swivel portion;

a motor connection receptacle formed in the motor portion to receive the motor connection shaft in rotatable engagement, wherein the motor is in fluid communication with the conduit.

24. The surgical instrument according to claim 21 further including a detent means in the angular swivel for releasably securing the motor in the aligned and angularly displaced positions.

25. In a surgical instrument for dissecting tissue, the surgical instrument including a conduit having a conduit axis defined through a terminal end thereof, and a fluid powered motor for rotating a dissecting tool, the motor having a longitudinal motor axis, the improvement comprising:

a central swivel portion including an inclined conduit face;

a conduit portion in fluid communication with the fluid conduit, the conduit portion including a mating inclined conduit face;

a connection shaft extending from the central swivel portion and normal to the mating inclined conduit face;

a conduit connection receptacle formed in the conduit portion to receive the conduit connection shaft in rotatable engagement, wherein the inclined conduit face and mating inclined conduit face are in sealing engagement;

a motor portion in fluid communication with the motor;

a motor connection shaft extending from the central swivel portion generally opposite the conduit connection shaft;

a motor connection receptacle formed in the motor portion to receive the motor connection shaft in rotatable engagement, wherein the motor is in fluid communication with the conduit; and fastener means for securing the conduit and motor connection shafts in the conduit and motor connection receptacles.

26. The surgical instrument according to claim 25 wherein the fastener means comprises a plurality of ball members disposed in a ball race formed between the motor connection shaft and receptacle and another ball race formed between the conduit connection shaft and receptacle.

27. The surgical instrument according to claim 25 further including a detent means between the conduit portion and the central swivel to releasably secure the motor in at least one position relative to the conduit.

28. The surgical instrument according to claim 25 further comprising:

a fluid inlet passage extending from the conduit, through the conduit portion, connection shafts of the central swivel, and motor portion and into the motor to supply pressurized fluid to the motor.

29. The surgical instrument according to claim 25 further comprising:

a plurality of conduit fluid exhaust passages formed in the conduit portion;

a plurality of motor fluid exhaust passages formed in the conduit portion;

an aperture formed in the central swivel portion to establish fluid communication between the motor and conduit fluid exhaust passages to exhaust fluid from the motor.

\* \* \* \* \*